United States Patent
Izvoztchikov et al.

(12) 
(10) Patent No.: US 6,521,186 B1
(45) Date of Patent: Feb. 18, 2003

(54) ARRANGEMENT FOR HOLDING HISTOLOGICAL AND BIOLOGICAL SPECIMENS

(75) Inventors: Ilia Borisovitch Izvoztchikov, St. Petersburg (RU); Serguei Petrovitch Mikhailov, St. Petersburg (RU)

(73) Assignee: Microm Laborgeräte GmbH (DE)

( * ) Notice: Subject to any disclaimer, the term of this patent is extended or adjusted under 35 U.S.C. 154(b) by 0 days.

(21) Appl. No.: 09/297,341

(22) PCT Filed: Oct. 22, 1997

(86) PCT No.: PCT/EP97/05829

§ 371 (c)(1),
(2), (4) Date: Aug. 30, 1999

(87) PCT Pub. No.: WO98/20379

PCT Pub. Date: May 14, 1998

(30) Foreign Application Priority Data

Nov. 1, 1996 (RU) .......................................... 96121684

(51) Int. Cl.⁷ .................................................. B01L 3/00
(52) U.S. Cl. .......................... 422/99; 156/363; 156/357; 156/521
(58) Field of Search ..................... 422/99, 50; 156/363, 156/357, 521, 556, 285; 427/2

(56) References Cited

U.S. PATENT DOCUMENTS

| 3,833,449 A | * | 9/1974 | Johnson ....................... 156/556 |
| 3,930,928 A | * | 1/1976 | Tapert ......................... 156/556 |
| 4,120,991 A | * | 10/1978 | Ornstein et al. ................ 427/2 |
| 4,171,241 A | * | 10/1979 | Henderson et al. ......... 156/556 |
| 4,203,797 A | * | 5/1980 | Stormby ..................... 156/521 |
| 4,428,793 A | * | 1/1984 | Sato et al. ................... 156/285 |
| 5,580,414 A | * | 12/1996 | Ljungmann ................. 156/363 |
| 5,700,346 A | * | 12/1997 | Edwards ..................... 156/357 |

* cited by examiner

*Primary Examiner*—Jill Warden
*Assistant Examiner*—Brian Sines

(57) ABSTRACT

A covering device places cover glasses on object carriers. The object carriers are held in a holder in a position inclined relative to the horizontal. The cover glasses are placed on the object carriers by a rotational movement. A pivot pin of the segment that places the cover glasses on the object carriers is mounted so as to be horizontally displaceable, such that when the cover glasses are positioned, they press on the object carriers in a rolling motion to prevent bubbles from forming in the specimen being mounted.

10 Claims, 2 Drawing Sheets

ARRANGEMENT FOR HOLDING HISTOLOGICAL AND BIOLOGICAL SPECIMENS

CROSS REFERENCE TO RELATED APPLICATIONS

Not applicable

STATEMENT REGARDING FEDERALLY SPONSORED RESEARCH OR DEVELOPMENT

Not applicable.

BACKGROUND OF THE INVENTION

1. Field of the Invention

This invention relates to an apparatus for mounting histological and biological specimens in the field of medicine. Among other things, it can be used for diagnostic apparatuses, and particularly in apparatuses for the mounting of histological and biological specimens in an optical medium for their microscopic investigation.

2. Discussion of Relevant Art

Specially prepared histological and biological specimens containing a stain are placed in an optically homogeneous medium and are investigated within a required time. Different materials, e.g., canada balsam or polystyrene, are used as the optical medium. Specimen mounting predominantly takes place manually. For this purpose, the specimen situated on the microscope slide is treated with a quantity of the material, respectively dissolved in xylene, and is then carefully mounted with the cover glass (G.I. Roskin, Mikroskopieverfahren (Microscopy Methods), Publisher: "Sovietskaya Nauka", Moscow, 1951, p. 152; G.A. Merkulow, "Short Course, Histopathologic Methods", Publisher "Medgis", Leningrad, 1951, p. 86; B. Romejs, Microscopy Methods, Publisher "IL", Moscow, 1953, pp. 191–192). Another method consists of applying a drop of resin dissolved in xylene to the cover glass of corresponding size. The microscope slide with the specimen is then carefully lowered until the specimen comes into contact with the drop of solution on the cover glass (R. Lill, Histopathologic Methods and Applied Histochemistry. Publisher: "Mir", Moscow, 1969, p. 85).

In all the cited articles it is mentioned that in manual mounting, air bubbles penetrate under the cover glass and distort the microscopic image. The air bubbles can be removed by pressing gently on the cover glass with the tip of a dissecting needle. B. Romejs believes that this procedure damages the preparation. Apart from this, manual specimen mounting is time-consuming, little productive, and moreover requires a qualified and experienced person.

In the existing mounting apparatuses, the Consul apparatus is closest to the present invention as regards performance; it is a product of the English company, Shandon. It includes a container for cover glasses, a holder for microscope slides, a metering apparatus for the solution of the optical medium, and a roller unit.

The holder for microscope slides consists of a few half frames attached to a rod and rotating in the plane situated at right angles to the rod. The roller unit in the Consul apparatus consists of a table with two rollers which are beneath the cover glass in the initial position. The table and the rollers can be displaced perpendicularly to the plane of the cover glass. The rollers can also draw back, with spring-mounted drive rods.

The microscope slides are placed on a rod which is displaced vertically. The microscope slide is placed in the working region by means of a rotational device. The container for the cover glasses and the solution metering device are fastened to a frame.

The Consul apparatus operates as follows: The pusher for cover glasses moves on the guide rails and pushes the lower glass out of the container into the working region. An amount of the solution of the optical medium is dropped from above onto the cover glass from the container in the working region. The rotary device displaces a half frame with a microscope slide and brings this into the working region above the cover glass, so that the specimen is turned downward. The table of the roller unit is raised and brings the cover glass quite near to the microscope slide. The pusher of the roller unit lifts the rollers until they come into contact with the cover glass. The spring-mounted drive rods thereafter draw back, and the rollers roll the upper surface of the cover glass. In this manner, the middle part of the cover glass is pressed by the table, and the side portions are rolled by the rollers. After this, the roller unit is lowered, and the rotary device brings the half frame with the mounted microscope slide into the initial position.

The Consul apparatus makes it possible to mount 400 specimens per hour. It can be successfully used in laboratories for histopathological investigations, because of its high performance.

The disadvantage of the Consul apparatus is the horizontal position of the cover glass and of the microscope slide during the pressing, due to which the removal of air bubbles from the optical medium is made difficult. This disadvantage is also present in the apparatuses described in U.S. Pat. No. 3,833,449, U.S. Pat. No. 4,171,241, U.S. Pat. No. 3,930,938, (German Utility Model) DE-U 295 14 506, or WO-A 94/14079.

SUMMARY OF THE INVENTION

The object of the present invention is to provide an apparatus in which air bubbles are avoided in the specimens being mounted.

This object is attained according to the invention by an apparatus for covering specimens placed on an object carrier with a cover glass. The apparatus includes a holder to receive object carriers, and a segment that applies a cover glass onto an object carrier that is received in the holder. The holder is constructed such that the normal to an object carrier received in the holder is inclined to the vertical by at least 45 degrees.

According to the present invention, a holder to receive, in a position inclined to the horizontal, the object carrier to be covered, and a device for the application of the respective cover glass to the object carrier which is aligned in an inclined attitude, are provided. It has been found that air bubbles can easily escape by means of an alignment of the object carrier inclined at at least 45° to the horizontal, and preferably vertically, during covering.

In other words, the normal to the object carrier is inclined to the vertical by at least 45 degrees.

In an advantageous embodiment example of the invention, the device for the application of the cover glasses is arranged to be rotatable or pivotable on the component which carries the mounting for the object carrier. With this device, the cover glasses are supplied by a rotary motion to the vertically aligned object carrier, and are pressed onto this. The axis of rotary or pivoting motion is then to be mounted horizontally movable, preferably against a resilient force. By the horizontally movable mounting of the axis of rotation or pivoting, the effect is attained that the line of maximum pressing force between the cover glass and the object carrier travels in a vertical direction during the rotary motion, so that the rotary or pivoting motion leads to the cover glass being rolled onto the object carrier. With the resilient mounting of the axis of rotation or pivoting, the pressing force is substantially determined by the spring force. In the basic position, i.e. before the application of the cover glass, the axis of rotation is horizontally offset from the vertical plane of the cover glass. During the rotary or pivoting motion, the rotation axis travels in the horizontal direction, and thus passes the vertical plane of the object carrier, and in the end position is finally positioned on the other side of the plane of the object carrier. For moving the cover glasses, the device for the application of cover glasses can simply reach through a window in a support plate which serves to receive the cover glasses. By means of a thrust device which serves for the transportation of individual cover glasses, the cover glasses can be brought out of a supply container into a position which covers the window in the support plate.

The apparatus according to the invention is preferably embodied as a manual device, wherein, for the rotary or pivoting motion for the application of the cover glasses and for the thrust device for the transportation of the cover glasses out of the supply container into the position covering the window in the support plate is constituted as a hand-operated lever or bar. It is thus possible to mechanically couple both drives together by simple means.

BRIEF DESCRIPTION OF THE DRAWINGS

Details of the invention will be described in further detail by means of the embodiment example shown in the Figures. In detail.

DETAILED DESCRIPTION OF PREFERRED EMBODIMENTS

Figure 1:
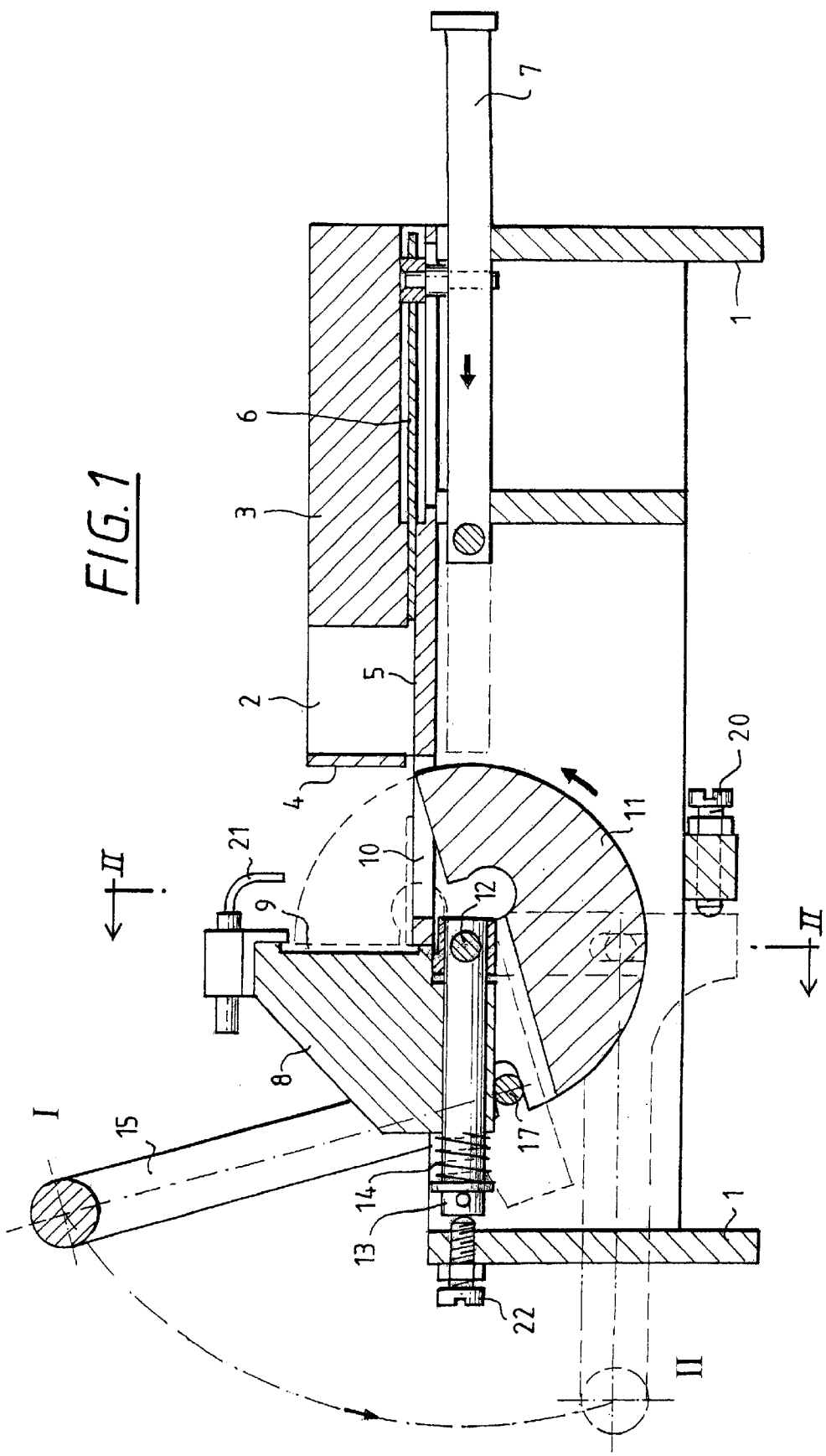
FIG. 1 shows a section through an apparatus according to the invention in a vertical plane.

The base frame of the apparatus is denoted by (1) in FIG. 1. The container for the cover glasses is arranged on this base frame. It consists of lateral bars (3), a lower support plate (5), and a vertical plate (4). The cavity defined between the lateral bars (3), the baseplate (5) and the vertical plate (4) serves as a container for cover glasses. The vertical plate (4) then forms the front wall of the container. The support plate (5) projects to the front side of the container below the vertical plate (4). A linear spacing is provided between the vertical plate (4) and the support plate (5), and is larger than the thickness of a cover glass, but smaller than the thickness of two cover glasses.

A pusher (6) is provided between the bars (3) and the support plate (5) and is guided, in a manner not shown, by the sidewalls of the container. The pusher (6) is constituted as a plate, the thickness of which is smaller than the thickness of a cover glass. The slider (6) can be operated by a drive rod.

A holder (8) is furthermore fixedly arranged on the base frame (1), to receive object carriers. This holder (8) has grooves in which an object carrier can be inserted vertically or nearly vertically. For object carriers inserted into the grooves (9), the surface normal of the object carrier glass is to have an angle of more than 45° to the vertical. The holder (8) thus adjoins the support plate (5) directly, so that an object carrier glass inserted into the holder (8) is positioned immediately adjacent to the support plate (5) but nearly perpendicular to it.

Furthermore a segment or device (11) is rotatably arranged on the base frame (1) and forms a device for supplying the cover glasses to an inserted object carder. The rotation axis (12) of the segment or device (11) is then angled horizontally and is itself further more linearly displaceable relative to the base frame (1). For this linear displaceability of the rotation axis (12), the rotation axis (12) is received in a preferably round component (13), a roller, which is itself furthermore received, horizontally displaceable against the force of a spring (14), on the be frame (1). The rotatable segment or device (11) can engage through a window (10) in the prolonged region of the support plate (5). The window (10) in the support plate (5) has therefor a width (b) which is smaller than the length (c) of a cover glass but is greater Man the thickness (d) of the segment or device (11).

Figure 2:
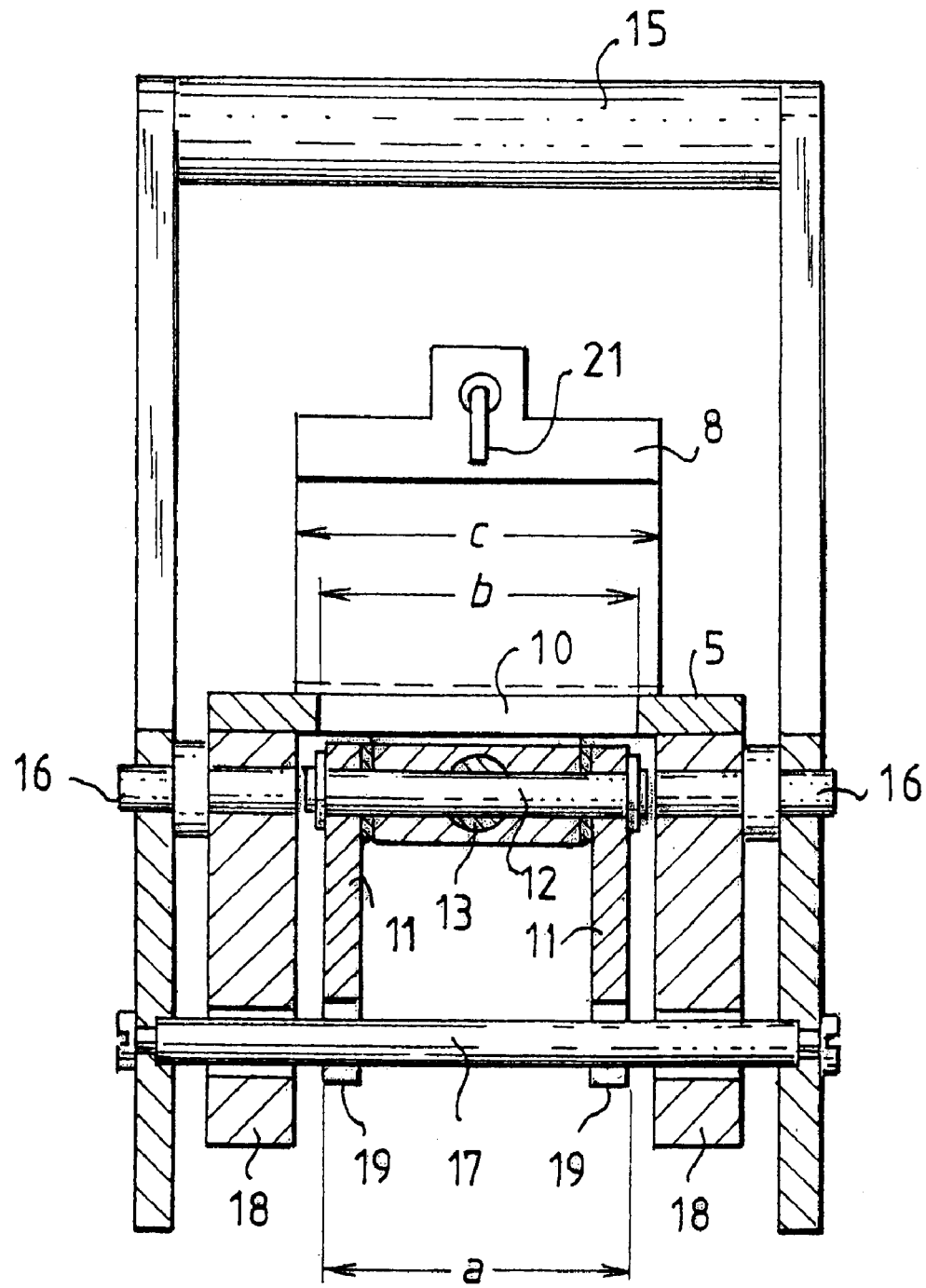
FIG. 2 shows a section through the arrangement of FIG. 1 in a plane perpendicular to FIG. 1.

The drive of the segment (11) can take place, for example, by means of a hand-operated drive frame (15) which is rotatably received on the base frame (1) by means of two half shafts (16) (FIG. 2). For a releasable coupling of the frame (15) to the segment (11), a pin (17) connecting the side portions of the frame (15) can be provided, and can engage in elongate slots (19) of the segment (11).

The embodiment example of the invention just described operates as follows: Firstly an object carrier glass with the specimen to be mounted is inserted vertically into the groove (9) of the holder (8). The alignment of the object carrier glass with the specimen should be such that the specimen is placed on the side of the object carrier glass which faces the container (2) for cover glasses. After this, the lowermost of the cover glasses situated in the container (2) is pushed out of the container (2) by actuation of the pusher (6), until the cover glass comes into contact with the object carrier glass. The cover glass which is pushed out thus comes to be situated above the window (10) of the support plate (5). After this, the pusher (6) returns to its initial position. A few drops of an optical medium are dispensed from a metering device (21) arranged above the container (8) onto the surface of the passed-through position shown by I in FIG. 1. With the rotation of the frame (15) thereby caused around the half shafts (16), the pin (17) of the frame (15) engages in the groove (19) of the segment (11). The segment (11) is thereby entrained, and rotates around the rotation axis (12). The segment (11) engages through the window (10) in the support plate (5) and lifts up the cover glass. With a further rotation of the segment (11), the cover glass is applied by a pivoting motion to the vertically aligned object carrier glass.

The rotation axis (12) of the segment (11) is first positioned on the side of the object carrier glass (9) remote from the specimen by means of corresponding setting of a stop screw (22) for the component (13). As a result, the cover glass first comes into contact with the lower edge of the object carrier glass. On further rotation of the segment (11) and the pressing force resulting therefrom between the cover glass and the object carrier glass, a horizontal movement of the rotation axis (12) of the segment (11) results, in that the component (13) is displaced horizontally against the force of the spring (14). The rotation axis (12) thus travels in the direction toward the container (2) for cover glasses, and passes through the plane of the object carrier glass. This horizontal movement of the rotation axis (12) has the result that the horizontal line of maximum pressing force travels from the lower edge to the upper edge of the object carrier glass and cover glass. A rolling motion is simulated by this travel of the line of maximum pressing force, and any air bubbles which may be included between the cover glass and the object carrier glass are thereby pressed out upward.

The movement of the frame (15) is continued until the frame (15) comes into contact with a second stop screw (20). This stop screw (20) is, again, set such that the abutment between the frame (15) and the stop screw (20) is reached in the position in which the line of maximum pressing force has reached the upper edge of the cover glass. The frame (15) is then located in the position II shown by dashed lines in FIG. 1. The frame (15) is then moved back toward its initial position. With this backward movement of the frame (15), there takes place by means of the action of the spring (14) a second rolling of the cover glass on the object carrier glass, but in the opposite direction this time, until the component (13) reaches the stop screw (22). With a further upward movement of the frame, the segment (11) returns to its initial position.

The vertical or nearly vertical position of the object carrier glass and of the cover glass during the rolling-on contributes to an effective removal of air bubbles from the optical medium. Trials with the apparatus according to the invention with histological specimens have shown that no formation of air bubbles was observed in 99% of the specimens investigated.

In the embodiment example shown in FIG. 1, two different manual drives, the frame (15) and the rod (7), are provided for the pusher (6) and the segment (11). It is however possible to couple the frame (15) and rod (7) together by means of a drive which can be uncoupled. It can thus be arranged that the drive (7) for the pusher (6) is actuated upon a movement to the right of the frame (15) out of the position denoted by I in FIG. 1. In the operation of such an alternative embodiment of the invention, the frame (15) is first moved to the right after insertion of an object carrier glass, so that a cover glass is positioned above the window (10) of the support plate (5). The frame is then moved back, as described hereinabove, into the position denoted by I, and in addition as far as the position denoted by II, so that covering of the specimen takes place. Furthermore, the frame (15) can also be coupled to a peristaltic pump for the metering device (21), so that when the frame (15) moves between the position denoted by I and the engagement of the pin (17) in the segment (11), the optical medium is automatically dispensed onto the surface of the cover glass.

What is claimed is:

1. An apparatus for covering specimens placed on an object carrier with a cover glass, comprising:
    a holder to receive object carriers, and
    a device that applies a cover glass onto an object carrier received in said holder, in which said holder is constructed such that the object carrier received in said holder is inclined to the horizontal by at least 45 degrees.

2. The apparatus according to claim 1, further comprising a carrying member carrying said holder, in which said device is arranged at least one of rotatably or pivotably on said carrying member.

3. The apparatus according to claim 2, in which the axis of rotation or pivoting of said device is mounted to be movable in a horizontal direction.

4. The apparatus according to claim 3, in which said axis of rotation or pivoting of said device is resiliently mounted.

5. The apparatus according to claim 1, in which said holder is arranged to receive object carriers in a vertical or nearly vertical alignment with the surface of an object.

6. The apparatus according to claim 5, in which before application of a cover glass axis of rotation or pivoting of said device is positioned with a horizontal offset with respect to a vertical plane of an object car.

7. The apparatus according to claim 1, in which said support plate includes a window and said deice engages said window.

8. The apparatus according to claim 1, further comprising a supply container for cover glasses and a thruster for transporting an individual cover glass into a position covering said window.

9. The apparatus according to claim 8, further comprising a common band drive that pivotably moves said device and said thruster.

10. The apparatus according to claim 1, further comprising a metering dispenser dispensing a solution onto a cover glass.

\* \* \* \* \*